US012085555B2

(12) United States Patent
Tabata et al.

(10) Patent No.: US 12,085,555 B2
(45) Date of Patent: Sep. 10, 2024

(54) DETERIORATION ESTIMATION DEVICE, DETERIORATION ESTIMATION METHOD, AND NON-TRANSITORY STORAGE MEDIUM THAT DETECTS A DEGREE OF DETERIORATION OF OIL BASED ON COLOR, HYDROGEN ION CONCENTRATION AND FOREIGN MATTER

(71) Applicant: TOYOTA JIDOSHA KABUSHIKI KAISHA, Toyota (JP)

(72) Inventors: Atsushi Tabata, Okazaki (JP); Ken Imamura, Toyota (JP); Kota Fujii, Nisshin (JP); Koichi Okuda, Toyota (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 535 days.

(21) Appl. No.: 17/369,494

(22) Filed: Jul. 7, 2021

(65) Prior Publication Data
US 2022/0018825 A1 Jan. 20, 2022

(30) Foreign Application Priority Data
Jul. 17, 2020 (JP) ................................ 2020-122584

(51) Int. Cl.
*G01N 33/28* (2006.01)
*F15B 19/00* (2006.01)
(Continued)

(52) U.S. Cl.
CPC ......... *G01N 33/2888* (2013.01); *F15B 19/00* (2013.01); *F16H 57/0405* (2013.01); *G01N 21/255* (2013.01); *G01N 33/2841* (2013.01)

(58) Field of Classification Search
CPC ... F15B 19/00; F16H 57/0405; G01N 21/255; G01N 33/2841; G01N 33/2888;
(Continued)

(56) References Cited

U.S. PATENT DOCUMENTS 4,203,725 A * 5/1980 Snowden, Jr. ..... G01N 33/2888
436/60
5,194,910 A * 3/1993 Kirkpatrick, Jr. .. G01N 21/3151
356/70

(Continued)

FOREIGN PATENT DOCUMENTS

JP 2009-276148 A 11/2009
JP 2011-214932 A 10/2011
(Continued)

*Primary Examiner* — Jay Patidar
(74) *Attorney, Agent, or Firm* — Oliff PLC

(57) ABSTRACT

A deterioration estimation device includes a storage device and an execution device. The storage device is configured to store mapping data defining a mapping that outputs an output variable indicating the degree of deterioration of oil when an input variable is input. The mapping includes, as the input variable, a color variable that is a variable indicating a color of the oil and a hydrogen ion variable that is a variable indicating a hydrogen ion concentration of the oil. The execution device is configured to execute an acquisition process that is a process of acquiring the input variable and a calculation process of inputting the input variable acquired through the acquisition process to the mapping to output a value of the output variable.

9 Claims, 4 Drawing Sheets

(51) Int. Cl.
*F16H 57/04* (2010.01)
*G01N 21/25* (2006.01)

(58) Field of Classification Search
CPC ............... G01N 15/0205; G01N 15/06; G01N 15/1429; G01N 15/1459; G01N 2015/0053; G01N 2015/0687; G01N 2015/0693; G01N 2015/1493; G01N 21/251
See application file for complete search history.

(56) References Cited

U.S. PATENT DOCUMENTS

| | | | |
|---|---|---|---|
| 8,664,966 B2 * | 3/2014 | Katafuchi | G01N 33/2876 |
| | | | 324/698 |
| 2011/0074452 A1 | 3/2011 | Katafuchi | |
| 2011/0239743 A1 * | 10/2011 | Yamashita | G01N 33/30 |
| | | | 73/53.05 |
| 2014/0365144 A1 * | 12/2014 | Dvorak | G01N 33/2888 |
| | | | 702/50 |
| 2016/0169859 A1 | 6/2016 | Yamashita | |
| 2018/0003618 A1 * | 1/2018 | Shinoda | G01N 21/251 |

FOREIGN PATENT DOCUMENTS

| | | |
|---|---|---|
| JP | 2013-117427 A | 6/2013 |
| JP | 2015-203642 A | 11/2015 |
| JP | 2016-114471 A | 6/2016 |

* cited by examiner

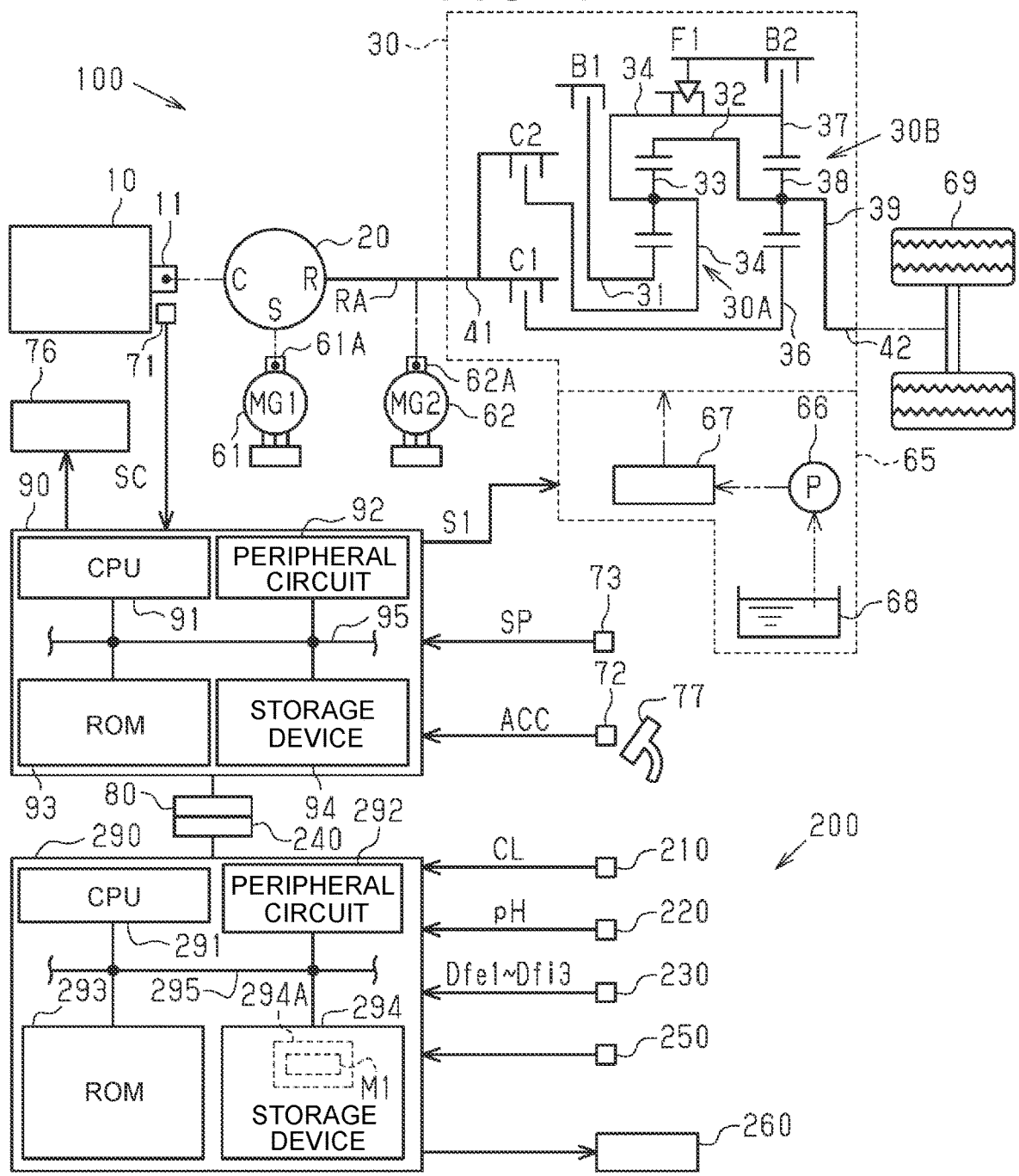

DETERIORATION ESTIMATION DEVICE, DETERIORATION ESTIMATION METHOD, AND NON-TRANSITORY STORAGE MEDIUM THAT DETECTS A DEGREE OF DETERIORATION OF OIL BASED ON COLOR, HYDROGEN ION CONCENTRATION AND FOREIGN MATTER

CROSS-REFERENCE TO RELATED APPLICATION

This application claims priority to Japanese Patent Application No. 2020-122584 filed on Jul. 17, 2020, incorporated herein by reference in its entirety.

BACKGROUND

1. Technical Field

The present disclosure relates to a deterioration estimation device, a deterioration estimation method, and a non-transitory storage medium.

2. Description of Related Art

Japanese Unexamined Patent Application Publication No. 2016-114471 (JP 2016-114471 A) describes a deterioration estimation device for estimating presence or absence of deterioration of oil in an automatic transmission. This deterioration estimation device estimates deterioration of oil when a condition that the temperature of the oil is equal to or higher than a predetermined temperature and the rotation speed of a specific rotating shaft in the automatic transmission is equal to or higher than a predetermined rotation speed continues for a predetermined period or longer. In estimating the deterioration of oil, the deterioration estimation device calculates the rate of increase in oil temperature from a certain period of time ago to the present time. When the rate of increase in oil temperature is equal to or higher than a threshold value, the deterioration estimation device determines that the oil has deteriorated.

SUMMARY

In the deterioration estimation device of JP 2016-114471 A, it is necessary to satisfy the condition related to the oil temperature and the like as a precondition for estimating the deterioration of oil. Therefore, the deterioration estimation device of JP 2016-114471 A cannot always execute the estimation of deterioration of oil, and the situation in which the estimation of deterioration of oil can be executed is limited.

A deterioration estimation device according to a first aspect of the present disclosure is applied to a vehicle equipped with a hydraulic device configured to supply oil and that is configured to estimate a degree of deterioration of the oil. The deterioration estimation device includes an execution device and a storage device. The storage device is configured to store mapping data defining a mapping that outputs an output variable indicating the degree of deterioration of the oil when an input variable is input. The mapping includes, as the input variable, a color variable that is a variable indicating a color of the oil and a hydrogen ion variable that is a variable indicating a hydrogen ion concentration of the oil. The execution device is configured to execute an acquisition process that is a process of acquiring the input variable and a calculation process of inputting the input variable acquired through the acquisition process to the mapping to output a value of the output variable.

The deterioration estimation device according to the first aspect of the present disclosure estimates the degree of deterioration of the oil, based on the color and the hydrogen ion concentration of the oil that are more likely to reflect the deterioration of the oil and less likely to be affected by the temperature of the oil and the usage condition of the oil. Therefore, it is possible to suppress the situation in which the deterioration estimation of the oil can be executed from being limited.

In the deterioration estimation device according to the first aspect of the present disclosure, the mapping may include, as the input variable, a foreign matter amount variable indicating an amount of foreign matter contained per unit volume of the oil. In the deterioration estimation device according to the first aspect of the present disclosure, a value having a high correlation with the degree of deterioration of oil, that is, the amount of foreign matter, is input to the mapping as the input variable. Thus, as the output variable, a value that accurately reflects the deterioration of oil can be obtained.

In the deterioration estimation device according to the first aspect of the present disclosure, the foreign matter amount variable may be the number of particles of the foreign matter contained per unit volume of the oil. In the deterioration estimation device according to the first aspect of the present disclosure, a parameter that is relatively easy to detect, such as the number of particles contained in the oil, is adopted as the foreign matter amount variable. Therefore, in estimating the degree of deterioration of oil, it is not necessary to use a special measuring device or perform a special work process.

In the deterioration estimation device according to the first aspect of the present disclosure, the mapping may include a first foreign matter amount variable and a second foreign matter amount variable as the input variable. The first foreign matter amount variable may indicate an amount of foreign matter having a particle size within a first range determined in advance, out of foreign matter contained per unit volume of the oil. The second foreign matter amount variable may indicate an amount of foreign matter having a particle size within a second range determined in advance as a range that is different from the first range, out of the foreign matter contained per unit volume of the oil.

With the deterioration estimation device according to the first aspect of the present disclosure, the degree of deterioration can be estimated based on not only the total amount of the foreign matter but also the distribution of the particle size of the foreign matter. Therefore, it is possible to accurately estimate the degree of deterioration of oil even when the particle size of the generated foreign matter changes as the deterioration of the oil progresses.

In the deterioration estimation device according to the first aspect of the present disclosure, the mapping may include a first foreign matter amount variable and a second foreign matter amount variable as the input variable. The first foreign matter amount variable may indicate an amount of foreign matter of a specific material, out of foreign matter contained per unit volume of the oil. The second foreign matter amount variable may indicate an amount of foreign matter of a material that is different from the specific material, out of the foreign matter contained per unit volume of the oil.

With the deterioration estimation device according to the first aspect of the present disclosure, the degree of deterioration can be estimated based on not only the total amount of the foreign matter but also the distribution of the types of materials of the foreign matter. Therefore, it is possible to accurately estimate the degree of deterioration of oil even when the distribution of the types of materials of the generated foreign matter changes as the deterioration of the oil progresses.

In the deterioration estimation device according to the first aspect of the present disclosure, the vehicle may include a transmission configured to be supplied with oil from the hydraulic device. The mapping may include, as the input variable, a shifting number variable indicating the number of times of shifting of the transmission since the oil is supplied to the vehicle. In the deterioration estimation device according to the first aspect of the present disclosure, the number of times of shifting of the transmission is taken into consideration in estimating the degree of deterioration of the oil. Therefore, the influence of wear powder generated by the wear of the components of the transmission can be incorporated into the estimation of the degree of deterioration of the oil.

In the deterioration estimation device according to the first aspect of the present disclosure, the mapping may include, as the input variable, a traveling distance variable indicating a traveling distance of the vehicle since the oil is supplied to the vehicle. With the deterioration estimation device according to the first aspect of the present disclosure, it is possible to estimate the degree of deterioration of oil in consideration of the value that is correlated with the degree of deterioration of oil, namely, the traveling distance.

In the deterioration estimation device according to the first aspect of the present disclosure, the mapping may include, as the input variable, a traveling time variable indicating a traveling time that a vehicle speed of the vehicle is higher than zero since the oil is supplied to the vehicle. With the deterioration estimation device according to the first aspect of the present disclosure, it is possible to estimate the degree of deterioration of oil in consideration of the value that is correlated with the degree of deterioration of oil, namely, the traveling time.

In the deterioration estimation device according to the first aspect of the present disclosure, the output variable may be a variable indicating a replacement timing at which the oil needs to be replaced. With the deterioration estimation device according to the first aspect of the present disclosure, the driver or the like of the vehicle can clearly grasp the replacement timing of oil.

In the deterioration estimation device according to the first aspect of the present disclosure, the output variable may be a variable that changes between a first value and a second value. The first value may be a value that indicates a state in which the oil has not deteriorated, and the second value may be a value that indicates a state in which the oil needs to be replaced and that is different from the first value. With the deterioration estimation device according to the first aspect of the present disclosure, it is easy to objectively grasp the degree of deterioration of oil as a numerical value.

A deterioration estimation method according to a second aspect of the present disclosure is applied to a vehicle equipped with a hydraulic device configured to supply oil. The deterioration estimation method is for estimating a degree of deterioration of the oil using a deterioration estimation device. The deterioration estimation method includes inputting, as an input variable, a color variable that is a variable indicating a color of the oil and a hydrogen ion variable that is a variable indicating a hydrogen ion concentration of the oil to the deterioration estimation device to calculate a value of an output variable. The deterioration estimation device is configured to store mapping data defining a mapping that outputs the output variable indicating the degree of deterioration of the oil when the input variable is input.

In the deterioration estimation method according to the second aspect of the present disclosure, the degree of deterioration of the oil is estimated, based on the color and the hydrogen ion concentration of the oil that are more likely to reflect the deterioration of the oil and less likely to be affected by the temperature of the oil and the usage condition of the oil. Therefore, it is possible to suppress the situation in which the deterioration estimation of the oil can be executed from being limited.

A non-transitory storage medium according to a third aspect of the present disclosure, as a deterioration estimation device that is applied to a vehicle equipped with a hydraulic device configured to supply oil and that is configured to estimate a degree of deterioration of the oil, stores instructions that are executable by one or more processors and that cause the one or more processors to perform functions. The functions include: acquiring, as an input variable, a color variable that is a variable indicating a color of the oil and a hydrogen ion variable that is a variable indicating a hydrogen ion concentration of the oil; and inputting the acquired input variable to the deterioration estimation device to calculate a value of an output variable. The deterioration estimation device is configured to store mapping data defining a mapping that outputs the output variable indicating the degree of deterioration of the oil when the input variable is input.

In the non-transitory storage medium according to the third aspect of the present disclosure, the degree of deterioration of the oil is estimated, based on the color and the hydrogen ion concentration of the oil that are more likely to reflect the deterioration of the oil and less likely to be affected by the temperature of the oil and the usage condition of the oil. Therefore, it is possible to suppress the situation in which the deterioration estimation of the oil can be executed from being limited.

BRIEF DESCRIPTION OF THE DRAWINGS

Features, advantages, and technical and industrial significance of exemplary embodiments of the present disclosure will be described below with reference to the accompanying drawings, in which like signs denote like elements, and wherein:

FIG. 1 is a schematic configuration diagram of a vehicle according to a first embodiment;

FIG. 2 is an explanatory diagram showing a relationship between shift stages and engaging elements in an automatic transmission according to the first embodiment;

DETAILED DESCRIPTION OF EMBODIMENTS

First Embodiment

Figure 3:
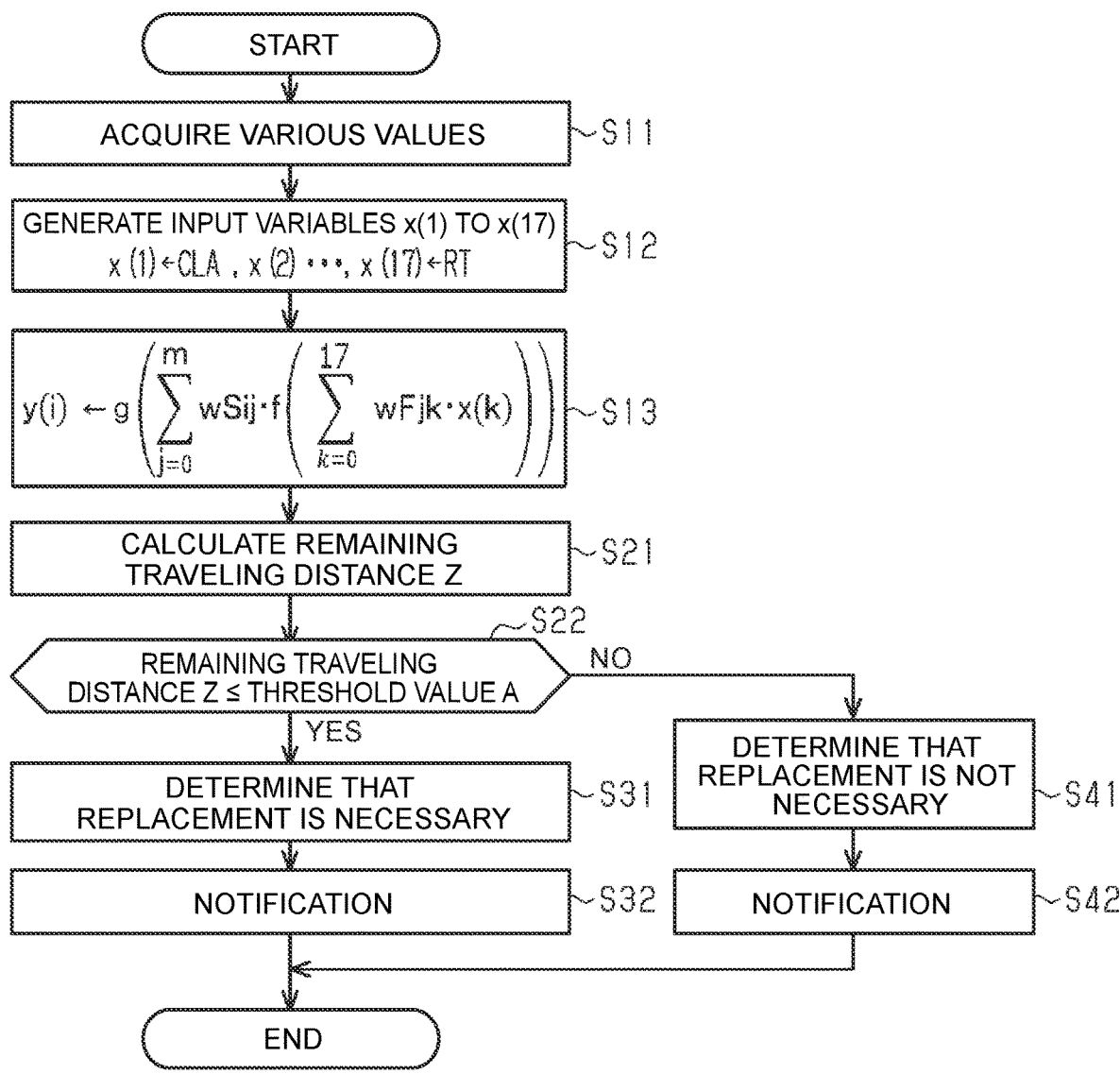
FIG. 3 is a flowchart showing an estimation control according to the first embodiment.

Hereinafter, an embodiment of the present disclosure will be described with reference to FIGS. 1 to 3. First, a schematic configuration of a vehicle 100 will be described.

As shown in FIG. 1, the vehicle 100 includes an internal combustion engine 10, a power split device 20, an automatic transmission 30, drive wheels 69, a hydraulic device 65, a first motor generator 61, and a second motor generator 62.

The power split device 20 is connected to a crankshaft 11 that is an output shaft of the internal combustion engine 10. The power split device 20 is a planetary gear mechanism having a sun gear S, a ring gear R, and a carrier C. The crankshaft 11 is connected to the carrier C of the power split device 20. A rotating shaft 61A of the first motor generator 61 is connected to the sun gear S. A rotating shaft 62A of the second motor generator 62 is connected to a ring gear shaft RA that is an output shaft of the ring gear R. An input shaft 41 of the automatic transmission 30 is also connected to the ring gear shaft RA. The right and left drive wheels 69 are connected to an output shaft 42 of the automatic transmission 30 via a differential gear (not shown).

When the internal combustion engine 10 is driven and torque is input from the crankshaft 11 to the carrier C of the power split device 20, the torque is split into torque on the sun gear S side and torque on the ring gear R side. When the first motor generator 61 operates as a motor and torque is input to the sun gear S of the power split device 20, the torque is split into torque on the carrier C side and torque on the ring gear R side.

When the second motor generator 62 operates as a motor and torque is input to the ring gear shaft RA, the torque is transmitted to the automatic transmission 30. When torque from the drive wheels 69 side is input to the second motor generator 62 via the ring gear shaft RA, the second motor generator 62 functions as a generator, and a regenerative braking force can be generated in the vehicle 100.

The automatic transmission 30 includes a first planetary gear mechanism 30A, a second planetary gear mechanism 30B, a first clutch C1, a second clutch C2, a first brake B1, a second brake B2, and a one-way clutch F1.

The first planetary gear mechanism 30A includes a sun gear 31, a ring gear 32, a pinion gear 33, and a carrier 34. The ring gear 32 is connected to the sun gear 31 via the pinion gear 33. The pinion gear 33 is supported by the carrier 34.

The sun gear 31 is connected to the first brake B1. The first brake B1 can be switched between an engaged state and a released state by a pressure of oil supplied to the first brake B1. Specifically, the pressure of oil supplied to the first brake B1 increases, so that the first brake B1 is switched from the released state to the engaged state. Then, when the first brake B1 is in the engaged state, the rotation of the sun gear 31 is braked.

The one-way clutch F1 is connected to the carrier 34. The one-way clutch F1 restricts rotation of the carrier 34 in one direction while permitting rotation of the carrier 34 in the other direction. That is, the one-way clutch F1 is switched between a restricting state that the one-way clutch F1 is restricting the rotation of the carrier 34 and a permitting state that the one-way clutch F1 is permitting the rotation of the carrier 34. Further, the carrier 34 is connected to the second brake B2. The second brake B2 can be switched between an engaged state and a released state by a pressure of oil supplied to the second brake B2, similarly to the first brake B1. When the second brake B2 is in the engaged state, the rotation of the carrier 34 is braked.

The second planetary gear mechanism 30B includes a sun gear 36, a ring gear 37, a pinion gear 38, and a carrier 39. The ring gear 37 is connected to the sun gear 36 via the pinion gear 38. The pinion gear 38 is supported by the carrier 39. The output shaft 42 is connected to the carrier 39.

In each of the planetary gear mechanisms configured as described above, the carrier 34 of the first planetary gear mechanism 30A is connected to the ring gear 37 of the second planetary gear mechanism 30B. The ring gear 32 of the first planetary gear mechanism 30A is connected to the carrier 39 of the second planetary gear mechanism 30B.

The sun gear 36 of the second planetary gear mechanism 30B is connected to the input shaft 41 via the first clutch C1. The first clutch C1 can be switched between an engaged state and a released state by a pressure of oil supplied to the first clutch C1. Specifically, the pressure of oil supplied to the first clutch C1 increases, so that the first clutch C1 is switched from the released state to the engaged state. When the first clutch C1 is brought into the engaged state, the sun gear 36 of the second planetary gear mechanism 30B rotates together with the input shaft 41.

The carrier 34 of the first planetary gear mechanism 30A is connected to the input shaft 41 via the second clutch C2. The second clutch C2 can be switched between an engaged state and a released state by a pressure of oil supplied to the second clutch C2, similarly to the first clutch C1. When the second clutch C2 is brought into the engaged state, the carrier 34 of the first planetary gear mechanism 30A rotates together with the input shaft 41. In the present embodiment, each of the first clutch C1, the second clutch C2, the first brake B1, and the second brake B2 is an engaging element.

As shown in FIG. 2, in the automatic transmission 30, the gear stage is switched based on a combination of the engaged state and the released state of the first clutch C1, the second clutch C2, the first brake B1, and the second brake B2, and a combination of the restricting state and the permitting state of the one-way clutch F1. In the automatic transmission 30, a total of five gear stages can be established, that is, four gear stages of "first gear" to "fourth gear" for traveling forward and one gear of "reverse gear" for traveling backward can be established.

Note that in FIG. 2, a sign "○" indicates that the engaging element such as the first clutch C1 is in the engaged state, and the one-way clutch F1 is in the restricting state. A sign "(○)" indicates that the second brake B2 is in the engaged state or the released state. Further, the blank indicates that the engaging element such as the first clutch C1 is in the released state and the one-way clutch F1 is in the permitting state. For example, when the gear stage of the automatic transmission 30 is second gear, the first clutch C1 and the first brake B1 are in the engaged state while the second clutch C2 and the second brake B2 are in the released state and the one-way clutch F1 is in the permitting state.

As shown in FIG. 1, the vehicle 100 is equipped with the hydraulic device 65. The hydraulic device 65 includes an oil pump 66, a hydraulic circuit 67, and an oil pan 68. Oil to be supplied to the automatic transmission 30 is stored in the oil pan 68. The oil pump 66 is a so-called mechanical oil pump that operates in response to torque of the crankshaft 11. The oil pump 66 supplies the oil stored in the oil pan 68 to the hydraulic circuit 67. The hydraulic circuit 67 includes a plurality of solenoid valves (not shown). The hydraulic circuit 67 adjusts the pressure of oil supplied to the first clutch C1, the second clutch C2, the first brake B1, and the second brake B2 by controlling the solenoid valves. That is, in the present embodiment, by controlling the solenoid valves of the hydraulic circuit 67, the engaged state and the released state of the engaging elements such as the first clutch C1 are controlled through the pressure of oil.

As shown in FIG. 1, the vehicle 100 is equipped with a crank angle sensor 71, an accelerator position sensor 72, a vehicle speed sensor 73, a display 76, and an accelerator pedal 77. The crank angle sensor 71 detects a crank angle SC that is a rotation angle of the crankshaft 11. The accelerator position sensor 72 detects an accelerator operation amount ACC that is an operation amount of the accelerator pedal 77 operated by a driver. The vehicle speed sensor 73 detects a vehicle speed SP that is the speed of the vehicle 100. The display 76 displays visual information to the driver of the vehicle 100 and the like. An example of the display 76 is a liquid crystal display provided at the driver's seat.

The vehicle 100 includes a control device 90. A signal indicating the crank angle SC is input to the control device 90 from the crank angle sensor 71. A signal indicating the accelerator operation amount ACC is input to the control device 90 from the accelerator position sensor 72. A signal indicating the vehicle speed SP is input to the control device 90 from the vehicle speed sensor 73. The control device 90 calculates an engine speed NE that is the rotation speed of the crankshaft 11 per unit time, based on the crank angle SC.

The control device 90 includes a central processing unit (CPU) 91, a peripheral circuit 92, a read only memory (ROM) 93, and a storage device 94. The CPU 91, the peripheral circuit 92, the ROM 93, and the storage device 94 are connected to each other through a bus 95 so as to be able to communicate with each other. Various programs are stored in the ROM 93 in advance for the CPU 91 to execute various kinds of control. The storage device 94 stores data including the accelerator operation amount ACC and the vehicle speed SP input to the control device 90 over a certain period of time. Here, the peripheral circuit 92 includes a circuit that generates a clock signal that defines the internal operation, a power supply circuit, a reset circuit, and the like.

The control device 90 is provided with a connector 80. The connector 80 has a general-purpose terminal group capable of bidirectional communication, and can communicate with other devices. In the present embodiment, the control device 90 can communicate with a deterioration estimation unit 200 described later via the connector 80.

The CPU 91 controls the internal combustion engine 10, the first motor generator 61, the second motor generator 62, the automatic transmission 30, and the like by executing various programs stored in the ROM 93. Specifically, the CPU 91 calculates a vehicle required output that is a required value of output required for the vehicle 100 to travel, based on the accelerator operation amount ACC and the vehicle speed SP. The CPU 91 determines a torque distribution of the internal combustion engine 10, the first motor generator 61, and the second motor generator 62 based on the vehicle required output. The CPU 91 controls the output of the internal combustion engine 10 and power running and regeneration of the first motor generator 61 and the second motor generator 62, based on the torque distribution of the internal combustion engine 10, the first motor generator 61, and the second motor generator 62.

The CPU 91 also calculates a target gear stage that is a gear stage targeted in the automatic transmission 30, based on the vehicle speed SP and the vehicle required output. The CPU 91 calculates a target pressure that is a target value of the pressure of oil supplied to the first clutch C1, the second clutch C2, the first brake B1, and the second brake B2, based on the target gear stage. Then, the CPU 91 outputs a control signal S1 to the hydraulic device 65 based on the target pressure. The hydraulic device 65 changes the pressure of oil supplied to the first clutch C1, the second clutch C2, the first brake B1, and the second brake B2 based on the control signal S1. For example, as shown in FIG. 2, when the gear stage of the automatic transmission 30 before the change is second gear, the first clutch C1 and the first brake B1 are in the engaged state while the second clutch C2 and the second brake B2 are in the released state and the one-way clutch F1 is in the permitting state. Here, when the target gear stage of the automatic transmission 30 is set to third gear, the pressure of oil supplied from the hydraulic device 65 to the second clutch C2 in response to the control signal S1 based on the target pressure of the second clutch C2 gradually increases, so that the second clutch C2 is switched from the released state to the engaged state. On the other hand, the pressure of oil supplied from the hydraulic device 65 to the first brake B1 gradually decreases in response to the control signal S1 based on the target pressure of the first brake B1, so that the first brake B1 is switched from the engaged state to the released state. As a result, the gear stage of the automatic transmission 30 is changed from second gear to third gear.

The CPU 91 calculates the number of times of shifting SN of the automatic transmission 30 since oil is supplied to the oil pan 68 in the vehicle 100 based on the target gear stage. Here, in the case where oil has not been replaced with new oil since the oil was supplied to the oil pan 68 at the time of manufacturing the vehicle 100, the time when the oil is supplied to the oil pan 68 in the vehicle 100 is the time of manufacturing the vehicle 100. When the oil in the oil pan 68 has been replaced with new oil, the time when the oil is supplied to the oil pan 68 in the vehicle 100 is the time when the oil is replaced with new oil. When the oil in the oil pan 68 is replaced with new oil, the number of times of shifting SN is reset. Further, the number of times of shifting SN is a total number of times of shifting of all shift types in the automatic transmission 30 including downshifts and upshifts, rather than the number of times of shifting of a specific shift type. Therefore, for example, when the gear stage of the automatic transmission 30 is changed from first gear to second gear and then changed from second gear to third gear, the number of times of shifting SN is two.

The CPU 91 calculates a traveling distance MI that the vehicle 100 has traveled since the oil was supplied to the oil pan 68 in the vehicle 100, based on the vehicle speed SP. Specifically, the CPU 91 calculates the traveling distance MI by time-integrating the vehicle speed SP. The CPU 91 also calculates a traveling time RT by integrating the time that the vehicle speed SP is larger than zero since the oil is supplied to the oil pan 68 in the vehicle 100, based on the vehicle speed SP. The storage device 94 stores data including the number of times of shifting SN, the traveling distance MI, and the traveling time RT.

Next, the deterioration estimation unit 200 will be described. The deterioration estimation unit 200 is installed in a place where maintenance of the vehicle 100 or the like is performed, for example, an automobile maintenance shop or the like. The deterioration estimation unit 200 includes an oil color detector 210, a hydrogen ion concentration detector 220, a foreign matter amount detector 230, an input device 250, a display 260, and a control device 290.

The oil color detector 210 detects an oil color CL that is a color of oil stored in the oil pan 68. An example of the oil color detector 210 is a so-called spectrophotometer that irradiates oil to be measured with light and measures the tristimulus values of the color based on the transmitted light. In the present embodiment, the oil color CL comprehensively represents a hue, a lightness, and a saturation of the oil.

The hydrogen ion concentration detector 220 detects the hydrogen ion concentration pH of oil stored in the oil pan 68. An example of the hydrogen ion concentration detector 220 is a sensor that performs measurement by immersing the probe in the oil to be measured.

The foreign matter amount detector 230 detects the particle size and the number of particles for each material in the foreign matter contained in the oil stored in the oil pan 68. Here, examples of the foreign matter contained in the oil include iron-based foreign matter mainly composed of iron, aluminum-based foreign matter mainly composed of aluminum, mineral-based foreign matter that is an inorganic crystalline substance, and fiber-based foreign matter that is a fibrous substance. An example of the foreign matter amount detector 230 is a so-called particle counter that is a measuring instrument that irradiates oil to be measured and containing foreign matter with light and measures the particle size and the number of particles of the foreign matter based on the scattered light. The particle counter sucks oil into the particle counter, and detects the particle size and the number of particles of the foreign matter contained in the oil when the oil passes through the detection unit.

The foreign matter amount detector 230 detects the presence of foreign matter, that is, the number of particles of foreign matter, based on the detection of scattered light. Further, the foreign matter amount detector 230 determines, based on the wavelength of the scattered light, whether the detected foreign matter is the iron-based foreign matter, whether the detected foreign matter is the aluminum-based foreign matter, whether the detected foreign matter is the mineral-based foreign matter, and whether the detected foreign matter is the fiber-based foreign matter. Further, the foreign matter amount detector 230 determines the particle size of the detected foreign matter based on the intensity of the scattered light.

The foreign matter amount detector 230 classifies the iron-based foreign matter, out of the detected foreign matter, by the particle size. In the present embodiment, the foreign matter amount detector 230 classifies the iron-based foreign matter into three, that is, iron-based foreign matter having a particle size of less than a first specified value, iron-based foreign matter having a particle size of equal to or more than the first specified value and less than a second specified value, and iron-based foreign matter having a particle size of equal to or more than the second specified value. The first specified value and the second specified value are determined in advance, and the second specified value is larger than the first specified value.

The foreign matter amount detector 230 multiplies the number of particles of the iron-based foreign matter having a particle size of less than the first specified value by a predetermined coefficient, so as to calculate a first particle number Dfe1 that represents the number of particles having a particle size of less than the first specified value among the iron-based foreign matter contained in the oil per unit volume. Similarly, the foreign matter amount detector 230 multiplies the number of particles of the iron-based foreign matter having a particle size of equal to or more than the first specified value and less than the second specified vale by a predetermined coefficient, so as to calculate a second particle number Dfe2 that represents the number of particles having a particle size of equal to or more than the first specified value and less than the second specified value among the iron-based foreign matter contained in the oil per unit volume. Also, the foreign matter amount detector 230 multiplies the number of particles of the iron-based foreign matter having a particle size of equal to or more than the second specified value by a predetermined coefficient, so as to calculate a third particle number Dfe3 that represents the number of particles having a particle size of equal to or more than the second specified value among the iron-based foreign matter contained in the oil per unit volume.

The foreign matter amount detector 230 also classifies the aluminum-based foreign matter, the mineral-based foreign matter, and the fiber-based foreign matter by the particle size in the same manner as the iron-based foreign matter. That is, the foreign matter amount detector 230 detects the number of particles having a particle size of less than the first specified value as a first particle number Da1, the number of particles having a particle size of equal to or more than the first specified value and less than the second specified value as a second particle number Da2, and the number of particles having a particle size of equal to or more than the second specified value as a third particle number Da3, among the aluminum-based foreign matter contained in the oil per unit volume. Also, the foreign matter amount detector 230 detects the number of particles having a particle size of less than the first specified value as a first particle number Dm1, the number of particles having a particle size of equal to or more than the first specified value and less than the second specified value as a second particle number Dm2, and the number of particles having a particle size of equal to or more than the second specified value as a third particle number Dm3, among the mineral-based foreign matter contained in the oil per unit volume. Further, the foreign matter amount detector 230 detects the number of particles having a particle size of less than the first specified value as a first particle number Dfi1, the number of particles having a particle size of equal to or more than the first specified value and less than the second specified value as a second particle number Dfi2, and the number of particles having a particle size of equal to or more than the second specified value as a third particle number Dfi3, among the fiber-based foreign matter contained in the oil per unit volume.

In the present embodiment, the foreign matter amount detector 230 treats the maximum width of each particle as the particle size. For example, in the case of an elliptical particle, the major axis of the particle is the particle diameter, and in the case of an elongated particle, the longitudinal length of the particle is the particle diameter.

The input device 250 is a device for inputting a command of an operator or the like who uses the deterioration estimation unit 200 to the control device 290. The input device 250 is, for example, a keyboard, a mouse, and the like. The display 260 is a device for transmitting information from the control device 290 to an operator and the like. The display 260 is, for example, a liquid crystal display.

The oil color detector 210, the hydrogen ion concentration detector 220, the foreign matter amount detector 230, the input device 250, and the display 260 are connected to the control device 290 via a cable and the like.

A signal indicating the oil color CL is input to the control device 290 from the oil color detector 210. A signal indicating the hydrogen ion concentration pH is input to the control device 290 from the hydrogen ion concentration detector 220. To the control device 290, signals indicating the first particle number Dfe1 to the third particle number Dfe3 for the iron-based foreign matter, the first particle number Da1 to the third particle number Da3 for the aluminum-based foreign matter, the first particle number Dm1 to the third particle number Dm3 for the mineral-based foreign matter, and the first particle number Dfi1 to the third particle number Dfi3 for the fiber-based foreign matter are input from the foreign matter amount detector 230.

The control device 290 calculates an oil color value CLA that is a numerical value indicating the oil color CL, based on the oil color CL. Specifically, the control device 290 stores a correspondence table in which numerical values are set in advance for each oil color. The control device 290 calculates the oil color value CLA by associating the oil color CL with the above correspondence table. In setting the above correspondence table, the oil is deteriorated by experiments and the like, and a plurality of colors that the oil can take when the oil deteriorates are grasped. Then, the above correspondence table is set by associating the colors that the oil can take when the oil deteriorates with the numerical values.

The control device 290 includes a central processing unit (CPU) 291, a peripheral circuit 292, a read only memory (ROM) 293, and a storage device 294. The CPU 291, the peripheral circuit 292, the ROM 293, and the storage device 294 are connected to each other through a bus 295 so as to be able to communicate with each other. Various programs are stored in the ROM 293 in advance for the CPU 291 to execute various kinds of control. Mapping data 294A is stored in the storage device 294 in advance. A mapping M1 defined by the mapping data 294A outputs an output variable indicating the degree of deterioration of oil when input variables are input. A specific description of the mapping M1 will be made later. The storage device 294 stores various kinds of data including the oil color value CLA, the hydrogen ion concentration pH, and the various numbers of particles over a fixed period of time. The peripheral circuit 292 includes a circuit that generates a clock signal that defines the internal operation, a power supply circuit, a reset circuit, and the like. In the present embodiment, the CPU 291 and the ROM 293 constitute an example of an execution device. The storage device 294 is an example of a storage device. The control device 290 functions as a deterioration estimation device. An example of the control device 290 is a personal computer.

The control device 290 is provided with a connector 240. The connector 240 has a general-purpose terminal group capable of bidirectional communication, and can communicate with other devices. In the present embodiment, for example, when the connector 240 of the deterioration estimation unit 200 is connected to the connector 80 of the vehicle 100 by an operator during maintenance of the vehicle 100, the control device 290 of the deterioration estimation unit 200 is enabled to communicate with the control device 90 of the vehicle 100. Then, when being instructed to receive data via the input device 250, the CPU 291 of the control device 290 accesses the storage device 94 of the control device 90 to acquire the number of times of shifting SN, the traveling distance MI, and the traveling time RT. The storage device 294 of the control device 290 stores the number of times of shifting SN, the traveling distance MI, and the traveling time RT.

Next, estimation control in which the CPU 291 estimates the degree of deterioration of oil stored in the oil pan 68 will be described. The CPU 291 executes a series of estimation control when being instructed to estimate the degree of deterioration of oil via the input device 250 by an operator or the like performing maintenance of the vehicle 100. The ROM 293 stores in advance an estimation program that is a program for executing the estimation control. The CPU 291 executes the estimation control by executing the estimation program stored in the ROM 293. It is assumed that, before execution of the estimation control, the number of times of shifting SN, the traveling distance MI, and the traveling time RT are stored in the storage device 294. It is also assumed that, before execution of the estimation control, the oil color value CLA, the hydrogen ion concentration pH, and the various numbers of particles are stored in the storage device 294.

Before execution of the estimation control, for example, an operator who performs maintenance of the vehicle 100 detects various values using the oil color detector 210, the hydrogen ion concentration detector 220, and the foreign matter amount detector 230. Specifically, the operator collects part of the oil stored in the oil pan 68 of the vehicle 100 at the time of maintenance of the vehicle 100 or the like. Then, the operator detects the oil color CL of the collected oil using the oil color detector 210. The operator also detects the hydrogen ion concentration pH of the collected oil using the hydrogen ion concentration detector 220. The operator also detects the various numbers of particles in the collected oil using the foreign matter amount detector 230. Then, the operator instructs the control device 290 to acquire various values via the input device 250, so that the detected oil color CL, the hydrogen ion concentration pH, and the various numbers of particles are input to the control device 290. As a result, before execution of the estimation control, the oil color value CLA based on the oil color CL, the hydrogen ion concentration pH, and the various numbers of particles are stored in the storage device 294.

As shown in FIG. 3, when the estimation control is started, the CPU 291 acquires various values in step S11 by accessing the storage device 294. Specifically, the CPU 291 acquires the oil color value CLA and the hydrogen ion concentration pH. The CPU 291 acquires the first particle number Dfe1 to the third particle number Dfe3 for the iron-based foreign matter, the first particle number Da1 to the third particle number Da3 for the aluminum-based foreign matter, the first particle number Dm1 to the third particle number Dm3 for the mineral-based foreign matter, and the first particle number Dfi1 to the third particle number Dfi3 for the fiber-based foreign matter. Further, the CPU 291 acquires the number of times of shifting SN, the traveling distance MI, and the traveling time RT. In the present embodiment, the process of step S11 is an acquisition process. After that, the CPU 291 advances the process to step S12.

In step S12, the CPU 291 generates the various values acquired in the process of step S11 as input variables $x(1)$ to $x(17)$ to the mapping M1 for estimating the degree of deterioration of oil stored in the oil pan 68.

The CPU 291 substitutes the oil color value CLA into the input variable $x(1)$. The CPU 291 substitutes the hydrogen ion concentration pH into the input variable $x(2)$. The CPU 291 substitutes the first particle number Dfe1 to the third particle number Dfe3 for the iron-based foreign matter into the input variables $x(3)$ to $x(5)$. The CPU 291 substitutes the first particle number Da1 to the third particle number Da3 for the aluminum-based foreign matter into the input variables $x(6)$ to $x(8)$. The CPU 291 substitutes the first particle number Dm1 to the third particle number Dm3 for the mineral-based foreign matter into the input variables $x(9)$ to $x(11)$. The CPU 291 substitutes the first particle number Dfi1 to the third particle number Dfi3 for the fiber-based foreign matter into the input variables $x(12)$ to $x(14)$. The CPU 291 substitutes the number of times of shifting SN into the input variable $x(15)$. The CPU 291 substitutes the traveling distance MI into the input variable $x(16)$. The CPU 291 substitutes the traveling time RT into the input variable $x(17)$. After that, the CPU 291 advances the process to step S13.

In the present embodiment, the input variable $x(1)$ is a color variable that is a variable indicating the color of oil.

The input variable x(2) is a hydrogen ion variable that is a variable indicating the hydrogen ion concentration of the oil. The input variables x(3) to x(14) are foreign matter amount variables that are variables indicating the amounts of foreign matter contained in the oil per unit volume. Further, when focusing on the iron-based foreign matter, the input variable x(3) is a first foreign matter amount variable indicating the amount of the foreign matter having a particle size within a predetermined first range, and the input variable x(4) is a second foreign matter amount variable indicating the amount of the foreign matter having a particle size within a predetermined second range that is set as a range different from the first range. Further, when focusing on the iron-based foreign matter and the aluminum-based foreign matter, the input variables x(3) to x(5) are first foreign matter amount variables indicating the amounts of foreign matter of a specific material, and the input variables x(6) to x(8) are second foreign matter amount variables indicating the amounts of foreign matter of a material different from the specific material. The input variable x(15) is a shifting number variable that is a variable indicating the number of times of shifting of the automatic transmission. The input variable x(16) is a traveling distance variable that is a variable indicating the traveling distance of the vehicle since the oil was supplied to the vehicle. The input variable x(17) is a traveling time variable indicating the traveling time that the vehicle speed of the vehicle is higher than zero since the oil is supplied to the vehicle.

In step S13, the CPU 291 inputs the input variables x(1) to x(17) generated in the process of step S12 and an input variable x(0) serving as a bias parameter to the mapping M1 defined by the mapping data 294A to calculate the value of an output variable y(i). After that, the CPU 291 advances the process to step S21.

An example of the mapping M1 defined by the mapping data 294A is a function approximator, specifically a fully connected feedforward neural network with one intermediate layer. Specifically, in the mapping M1 defined by the mapping data 294A, the values of the nodes in the intermediate layer are determined by substituting, into the activation function f, each of the "m" values obtained by conversion of the input variables x(1) to x(17) and the input variable x(0) serving as a bias parameter by the linear mapping defined by a coefficient wFjk (j=1 to m, k=0 to 17). Further, the output variable y(1) is determined by substituting, into the activation function g, the values obtained by conversion of the values of the nodes in the intermediate layer by the linear mapping defined by a coefficient wSij (i=1). The output variable y(1) is a variable indicating the distance that the vehicle 100 can travel before oil stored in the oil pan 68 is replaced with new oil. Here, the distance that the vehicle 100 can travel becomes shorter as oil deteriorates. Therefore, the output variable y(1) can be said to be a value indicating the degree of deterioration of oil. Further, the output variable y(1) is an example of a variable indicating a replacement timing at which oil needs to be replaced. The larger the output variable y(1), the longer the distance that the vehicle 100 can travel. In the present embodiment, the processes of steps S12 and S13 constitute a calculation process. In the present embodiment, an example of the activation function f is a rectified linear unit (ReLU) function. An example of the activation function g is a sigmoid function.

The mapping M1 defined by the mapping data 294A is generated as follows, for example. First, before the shipment of the produced vehicles 100, a prototype vehicle is run in various states, for example, to deteriorate oil after new oil is supplied to the oil pan 68 until the oil needs to be replaced. At this time, various values related to the oil before the replacement becomes necessary and various values related to the oil when the replacement becomes necessary are acquired. Then, the various values related to the oil before the replacement becomes necessary and the various values related to the oil after the replacement becomes necessary are learned as teacher data so that a trained mapping M1 is generated.

In step S21, the CPU 291 calculates a remaining traveling distance Z that is a distance that the vehicle 100 can travel without replacement of oil, based on the output variable y(1). In the present embodiment, the CPU 291 calculates the remaining traveling distance Z as a longer distance as the output variable y(1) is larger. After that, the CPU 291 advances the process to step S22.

In step S22, the CPU 291 determines whether the remaining traveling distance Z is equal to or less than a predetermined threshold value A. Here, the remaining traveling distance Z becomes shorter as oil deteriorates. Thus, the threshold value A is set as a value for determining whether the remaining traveling distance Z becomes short and the oil needs to be replaced soon, that is, several tens of kilometers to several hundred kilometers, for example. In step S22, when the CPU 291 determines that the remaining traveling distance Z is equal to or less than the threshold value A (S22: YES), the CPU 291 advances the process to step S31.

In step S31, the CPU 291 determines that the oil stored in the oil pan 68 needs to be replaced with new oil. After that, the CPU 291 advances the process to step S32. In step S32, the CPU 291 outputs, to the display 260, a signal for causing the display 260 to indicate that it is necessary to replace the oil with new oil. The CPU 291 also outputs, to the display 260, a signal for causing the display 260 to display the remaining traveling distance Z. After that, the CPU 291 ends the present estimation control.

In step S22, when the CPU 291 determines that the remaining traveling distance Z is more than the threshold value A (S22: NO), the CPU 291 advances the process to step S41. In step S41, the CPU 291 determines that the oil stored in the oil pan 68 need not be replaced with new oil. After that, the CPU 291 advances the process to step S42. In step S42, the CPU 291 outputs, to the display 260, a signal for causing the display 260 to indicate that it is not necessary to replace the oil with new oil. The CPU 291 also outputs, to the display 260, a signal for causing the display 260 to display the remaining traveling distance Z. After that, the CPU 291 ends the present estimation control.

Operations and effects of the present embodiment will be described. (1) In the vehicle 100 of the above embodiment, as the oil deteriorates, the oil color CL, which is the color of oil, changes with deterioration of the oil. For example, as the oil deteriorates, the color of oil changes from light brown to dark brown. Further, as the oil deteriorates, the hydrogen ion concentration pH of the oil changes with the deterioration of the oil. The oil color CL and the hydrogen ion concentration pH are not easily affected by the usage state of oil such as the operating state of the vehicle 100 and the operating state of the automatic transmission 30. Therefore, in the present embodiment, in estimating the deterioration of oil, the oil color CL and the hydrogen ion concentration pH are acquired, and the deterioration of oil is estimated from the oil color value CLA based on the oil color CL and the hydrogen ion concentration pH. Thereby, the degree of deterioration of oil can be estimated regardless of the driving state of the vehicle 100, even when the automatic transmission 30 and the like of the vehicle 100 is not operating. It should be noted that there is a possibility that a simple relationship such as a linear relationship cannot be obtained between the oil color CL or the hydrogen ion concentration pH and the deterioration of oil. Even in such a case, by estimating the degree of deterioration of oil using the learned mapping M1, it is possible to accurately estimate the degree of deterioration.

(2) When the first clutch C1 or the like in the automatic transmission 30 is switched from the released state to the engaged state, wear powder is generated due to wear of the friction member of the first clutch C1 or the like, and the wear powder may mix in the oil as foreign matter. The total amount of foreign matter contained in the oil tends to increase as the deterioration of the oil progresses.

To the mapping M1 defined by the mapping data 294A, values indicating the first particle number Dfe1 for the iron-based foreign matter and the like are input as the foreign matter amount variables. That is, values having a high correlation with the degree of deterioration of oil, that is, the amounts of foreign matter, are input to the mapping M1 as the input variables. Thus, as the output variable, a value that accurately reflects the deterioration of oil can be obtained.

(3) Since the foreign matter contained in the oil is a particulate solid having various shapes, it is difficult to accurately detect the volume of the foreign matter contained in the oil per unit volume, for example. In contrast, the number of particles of the foreign matter contained in the oil per unit volume is easier to be detected than the volume of the foreign matter contained in the oil per unit volume. Therefore, as the foreign matter amount variable to be input to the mapping M1, the number of particles of the foreign matter contained in the oil per unit volume is adopted. Thus, in estimating the degree of deterioration of oil, it is not necessary to use, for example, a special measuring device or perform a special work process in order to detect the number of particles of the foreign matter.

(4) The particle size of the foreign matter contained in the oil may change with the degree of deterioration of the oil. For example, immediately after the automatic transmission 30 is manufactured, the particles generated in the manufacturing process of the automatic transmission 30 appear in the oil as foreign matter, so the particle size of the foreign matter is relatively large. On the other hand, as the automatic transmission 30 is used, wear powder associated with the engagement of the engaging elements appears in the oil, so the particle size of the foreign matter is relatively small. Thus, as the automatic transmission 30 is used, in other words, as the oil deteriorates, the distribution of the particle size of the foreign matter changes. Thus, to the mapping M1 defined by the mapping data 294A, the foreign matter amount roughly classified by the particle size is input. Thereby, the degree of deterioration of oil can be estimated in consideration of the distribution of the particle size of the foreign matter. As a result, it is possible to accurately estimate the degree of deterioration of oil even when the particle size of the foreign matter changes as the deterioration of the oil progresses.

(5) The foreign matter contained in the oil may include not only the iron-based foreign matter but also the foreign matter of different materials such as aluminum. In this case, as the deterioration of the oil progresses, the distribution of the amount of iron-based foreign matter and the amount of aluminum-based foreign matter, that is, for example, the ratio between the amount of the iron-based foreign matter and the amount of the aluminum-based foreign matter may change.

Thus, to the mapping M1, not only the first particle number Dfe1 to the third particle number Dfe3 for the iron-based foreign matter, but also the first particle number Da1 to the third particle number Da3 for the aluminum-based foreign matter, the first particle number Dm1 to the third particle number Dm3 for the mineral-based foreign matter, and the first particle number Dfi1 to the third particle number Dfi3 for the fiber-based foreign matter are input. This makes it possible to estimate the degree of deterioration of oil in accordance with the distribution of types of materials of the foreign matter. As a result, it is possible to accurately estimate the degree of deterioration of oil even when the distribution of the types of materials of the generated foreign matter changes as the deterioration of the oil progresses.

(6) As the number of times of shifting SN of the automatic transmission 30 increases, the number of times the engaging element is switched from the released state to the engaged state increases. Also, as the number of times of engagement in which the engaging element is brought into the engaged state increases, the number of times frictional heat is generated in the engaging element increases, so the deterioration of the oil tends to progress. Further, as the number of time of engagement increases, the chance that wear powder is generated from the friction member of the engaging element increases, so the deterioration of the oil tends to progress due to the wear powder.

Therefore, the variable indicating the number of times of shifting SN is input as the input variable to the mapping M1 defined by the mapping data 294A. Accordingly, the number of times of shifting SN of the automatic transmission 30 is taken into consideration when the degree of deterioration of oil is estimated. As a result, it is possible to estimate the degree of deterioration of oil while incorporating the influence of generation of frictional heat and wear powder at the engaging element.

(7) The temperature of oil stored in the oil pan 68 while the vehicle 100 is traveling tends to be higher than that while the vehicle 100 is not traveling. The longer the traveling distance MI of the vehicle 100, the greater the chance that the temperature of oil stored in the oil pan 68 rises. As a result, the deterioration of oil tends to progress.

Thus, the variable indicating the traveling distance MI is input as the input variable to the mapping M1 defined by the mapping data 294A. Accordingly, it is possible to estimate the degree of deterioration of oil in consideration of the value that is correlated with the degree of deterioration of oil, namely, the traveling distance MI.

(8) The longer the traveling time RT of the vehicle 100, the longer the period during which the temperature of oil stored in the oil pan 68 is high. As a result, the deterioration of oil tends to progress. Thus, the variable indicating the traveling time RT is input as the input variable to the mapping M1 defined by the mapping data 294A. Accordingly, it is possible to estimate the degree of deterioration of oil in consideration of the value that is correlated with the degree of deterioration of oil, namely, the traveling time RT.

(9) As the output variable y(1) of the mapping M1 defined by the mapping data 294A, a variable is output that indicates the distance that the vehicle 100 can travel before replacement of oil stored in the oil pan 68 with new oil. Then, on the display 260, not only the need to replace the oil, but also the remaining traveling distance Z based on the output variable y(1) is displayed. Accordingly, an operator or the like who performs the maintenance of the vehicle 100 can clearly grasp the replacement timing of oil from the displayed remaining traveling distance Z.

Second Embodiment

Hereinafter, a second embodiment of the present disclosure will be described with reference to FIGS. 4 and 5. The present embodiment is different from the first embodiment in that the control device 90 functions as the deterioration estimation device instead of the control device 290 in the deterioration estimation unit 200. In the description of the second embodiment, the differences from the first embodiment will be mainly described, and the same reference signs will be given to the same configurations as those of the first embodiment, and the description thereof will be omitted or simplified.

Figure 4:
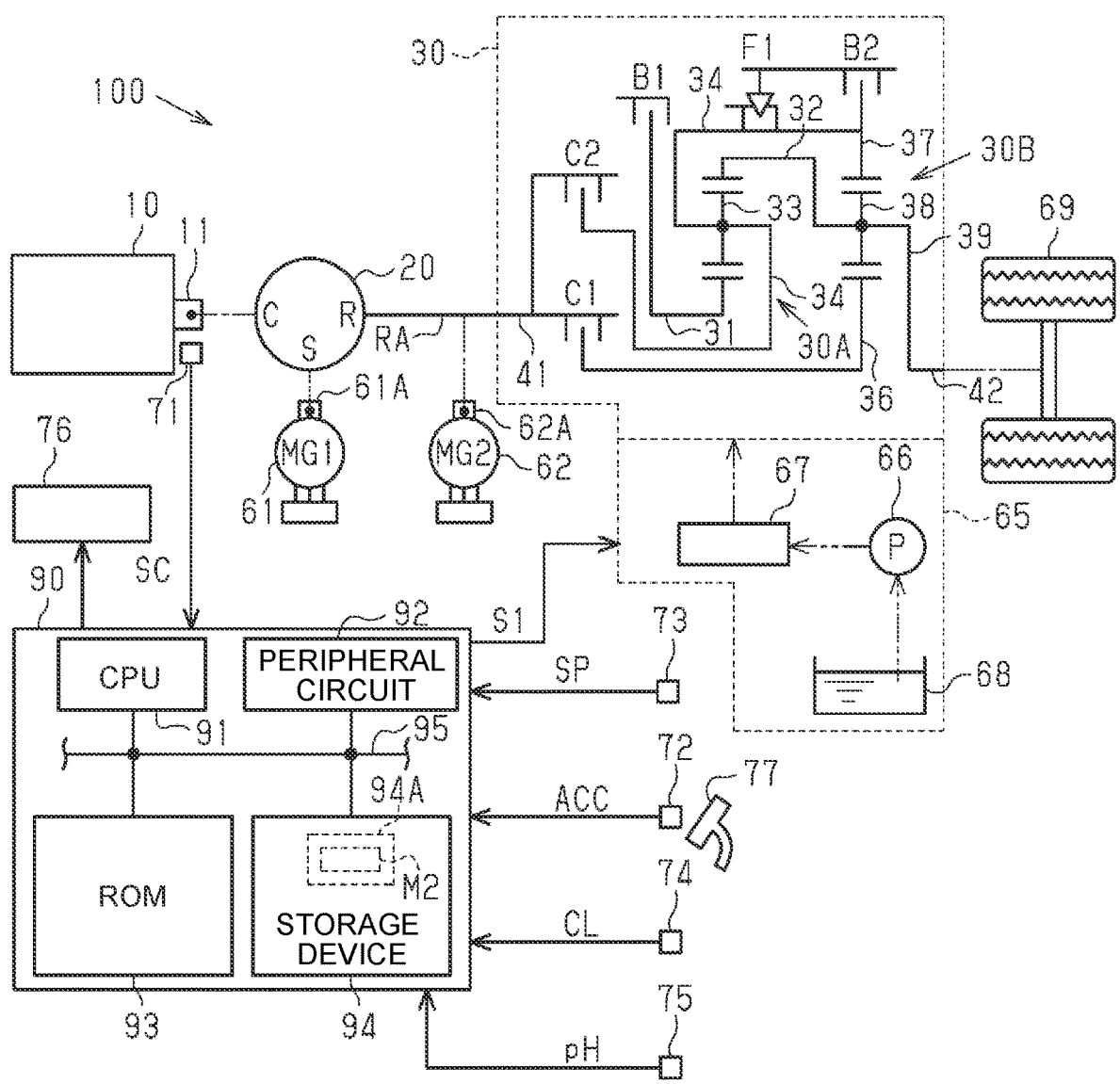
FIG. 4 is a schematic configuration diagram of a vehicle according to a second embodiment.

As shown in FIG. 4, the vehicle 100 includes an oil color detector 74 and a hydrogen ion concentration detector 75. The oil color detector 74 detects the oil color CL that is a color of oil stored in the oil pan 68. The oil color detector 74 is provided in the vicinity of the oil pan 68. An example of the oil color detector 74 is a so-called color sensor that is a sensor that irradiates oil to be measured with light and detects the tristimulus values of the color based on the reflected light. The hydrogen ion concentration detector 75 detects the hydrogen ion concentration pH of oil stored in the oil pan 68. The hydrogen ion concentration detector 75 is provided in the vicinity of the oil pan 68. An example of the hydrogen ion concentration detector 75 is a sensor that performs measurement by immersing a probe in the oil to be measured and that has the tip of the probe disposed in the oil pan 68.

A signal indicating the oil color CL is input to the control device 90 from the oil color detector 74. A signal indicating the hydrogen ion concentration pH is input to the control device 90 from the hydrogen ion concentration detector 75.

The control device 90 calculates an oil color value CLA that is a numerical value indicating the oil color CL, based on the oil color CL. Specifically, the control device 90 stores a correspondence table in which numerical values are set in advance for each oil color. The control device 90 calculates the oil color value CLA by associating the oil color CL with the above correspondence table.

Mapping data 94A is stored in advance in the storage device 94. A mapping M2 defined by the mapping data 94A outputs an output variable indicating the degree of deterioration of oil when input variables are input. A specific description of the mapping M2 will be made later. The storage device 94 stores various kinds of data including the oil color value CLA and the hydrogen ion concentration pH over a fixed period of time. In the present embodiment, the CPU 91 and the ROM 93 constitute an example of the execution device. The storage device 94 is an example of the storage device.

Next, estimation control in which the CPU 91 estimates the degree of deterioration of oil stored in the oil pan 68 will be described. The CPU 91 executes estimation control at predetermined cycles determined in advance from the time when the CPU 91 starts operation to the time when the CPU ends the operation. The ROM 93 stores in advance an estimation program that is a program for executing the estimation control. The CPU 91 executes the estimation control by executing the estimation program stored in the ROM 93.

Figure 5:
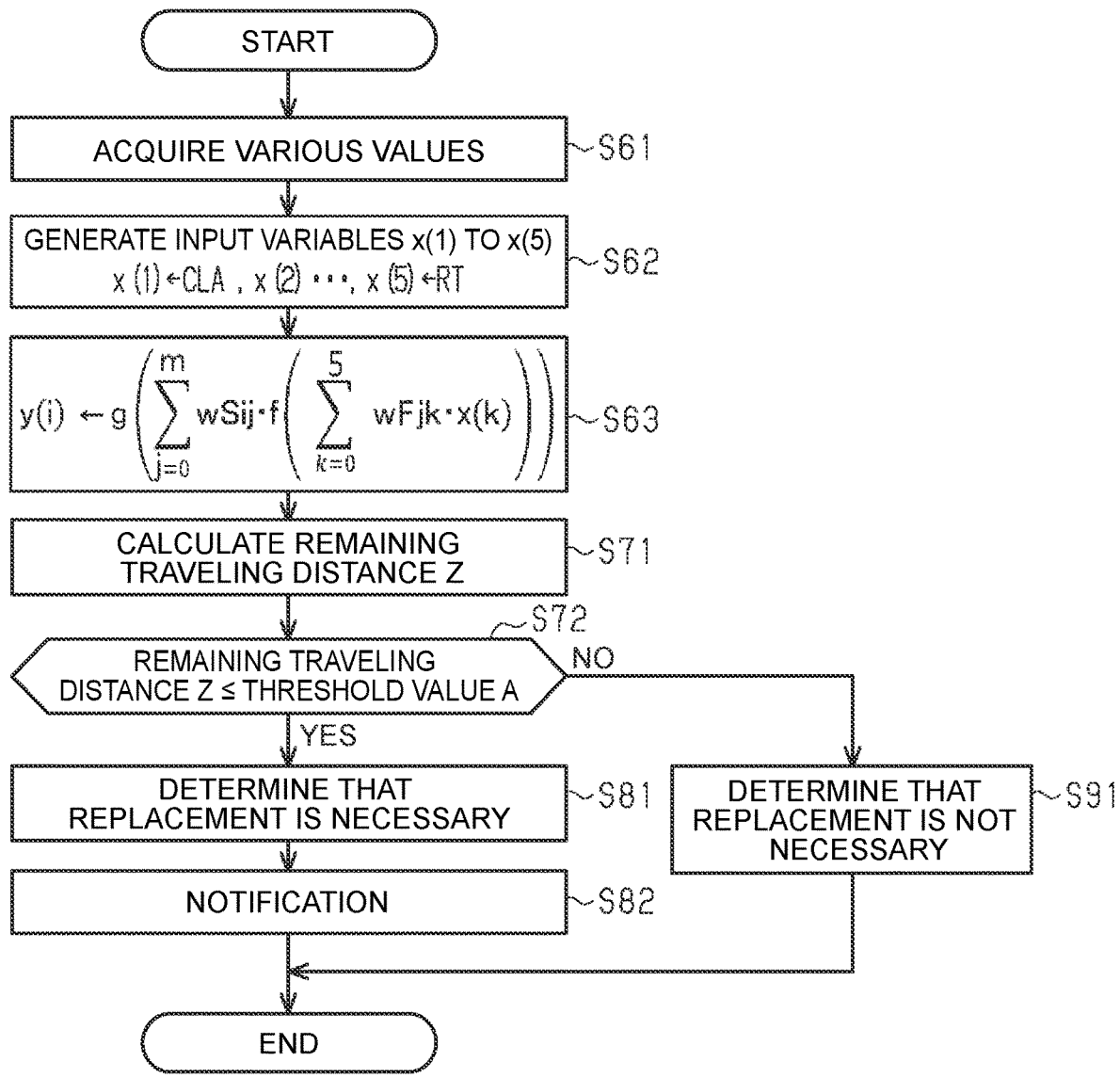
FIG. 5 is a flowchart showing an estimation control according to the second embodiment.

As shown in FIG. 5, when the estimation control is started, the CPU 91 acquires various values in step S61 by accessing the storage device 94. Specifically, the CPU 91 acquires the oil color value CLA, the hydrogen ion concentration pH, the number of times of shifting SN, the traveling distance MI, and the traveling time RT. In the present embodiment, the process of step S61 is an acquisition process. After that, the CPU 91 advances the process to step S62.

In step S62, the CPU 91 generates the various values acquired in the process of step S61 as input variables x(1) to x(5) to the mapping M2 for estimating the degree of deterioration of oil stored in the oil pan 68.

The CPU 91 substitutes the oil color value CLA into the input variable x(1). The CPU 91 substitutes the hydrogen ion concentration pH into the input variable x(2). The CPU 91 substitutes the number of times of shifting SN into the input variable x(3). The CPU 91 substitutes the traveling distance MI into the input variable x(4). The CPU 91 substitutes the traveling time RT into the input variable x(5). After that, the CPU 91 advances the process to step S63.

In the present embodiment, the input variable x(1) is a color variable that is a variable indicating the color of oil. The input variable x(2) is a hydrogen ion variable that is a variable indicating the hydrogen ion concentration of the oil. The input variable x(3) is a shifting number variable that is a variable indicating the number of times of shifting of the automatic transmission. The input variable x(4) is a traveling distance variable that is a variable indicating the traveling distance of the vehicle since the oil was supplied to the vehicle. The input variable x(5) is a traveling time variable indicating the traveling time that the vehicle speed of the vehicle is higher than zero since the oil is supplied to the vehicle.

In step S63, the CPU 91 inputs the input variables x(1) to x(5) generated in the process of step S62 and an input variable x(0) serving as a bias parameter to the mapping M2 defined by the mapping data 94A to calculate the value of an output variable y(i). After that, the CPU 91 advances the process to step S71.

An example of the mapping M2 defined by the mapping data 94A is a function approximator, specifically a fully connected feedforward neural network with one intermediate layer. The mapping M2 is the same as the mapping M1 in the first embodiment except that the number and types of input variables are different. Therefore, detailed description thereof will be omitted.

In step S71, the CPU 91 calculates the remaining traveling distance Z that is a distance that the vehicle 100 can travel without replacement of oil, based on the output variable y(1). The CPU 91 calculates the remaining traveling distance Z as a longer distance as the output variable y(1) is larger. After that, the CPU 91 advances the process to step S72.

In step S72, the CPU 91 determines whether the remaining traveling distance Z is equal to or less than a predetermined threshold value A. The threshold value A in the second embodiment is the same as the threshold value A in the first embodiment. In step S72, when the CPU 91 determines that the remaining traveling distance Z is equal to or less than the threshold value A (S72: YES), the CPU 91 advances the process to step S81.

In step S81, the CPU 91 determines that the oil stored in the oil pan 68 needs to be replaced with new oil. After that, the CPU 91 advances the process to step S82. In step S82, the CPU 91 outputs, to the display 76, a signal for causing the display 76 to indicate that it is necessary to replace the oil with new oil. The CPU 91 also outputs, to the display 76, a signal for causing the display 76 to display the remaining traveling distance Z. After that, the CPU 91 ends the present estimation control.

In step S72, when the CPU 91 determines that the remaining traveling distance Z is more than the threshold value A (S72: NO), the CPU 91 advances the process to step S91. In step S91, the CPU 91 determines that the oil stored in the oil pan 68 need not be replaced with new oil. After that, the CPU 91 ends the present estimation control.

Operations and effects of the present embodiment will be described. In the present embodiment, in addition to the above-mentioned effects (1) and (6) to (8), the following effects (10) and (11) can be obtained.

(10) As the output variable y(1) of the mapping M2 defined by the mapping data 94A, a variable indicating the distance that the vehicle 100 can travel before replacement of oil stored in the oil pan 68 with new oil is output. Then, on the display 76, not only the need to replace the oil, but also the remaining traveling distance Z based on the output variable y(1) is displayed. Accordingly, a driver and the like of the vehicle 100 can clearly grasp the replacement timing of oil from the displayed remaining traveling distance Z.

(11) In the above embodiment, the control device 90 of the vehicle 100 functions as the deterioration estimation device. Therefore, it is possible to obtain information on whether to change the oil without going to a specific place such as an automobile maintenance shop.

Other Embodiments

The present embodiment can be modified to be implemented as follows. The present embodiment and modifications to be described below may be carried out in combination within a technically consistent range.

About Color Variable

In the first embodiment and the second embodiment, the color variable is not limited to the example of the above embodiments. For example, the color variable does not have to be a variable that comprehensively represents a hue, a lightness, and a saturation of oil, and may be a variable that represents any one of the hue, the lightness, and the saturation of oil.

For example, when the color of new oil supplied to the oil pan 68 is transparent light brown, the more the oil deteriorates, the less transparent the oil may become. In this case, the color variable may be a variable indicating the transparency of the oil.

About Hydrogen Ion Variable

In the first embodiment and the second embodiment, the hydrogen ion variable is not limited to the example of the above embodiments. For example, as the hydrogen ion variable, a variable that changes stepwise in accordance with the hydrogen ion concentration pH may be adopted. As a specific example, a variable that becomes "0" when the hydrogen ion concentration pH is less than a predetermined constant value and becomes "1" when the hydrogen ion concentration pH is equal to or more than the predetermined constant value may be input to the mapping as the hydrogen ion variable.

About Other Input Variables

In the first embodiment and the second embodiment, the input variables are not limited to the examples of the above embodiments. For example, the material of the wear powder generated from the friction member changes depending on the material of the friction member of the engaging element in the automatic transmission 30, so the material of the foreign matter contained in the oil changes. Thus, the amount of foreign matter of other materials, in place of or in addition to the iron-based foreign matter, the aluminum-based foreign matter, the mineral-based foreign matter, and the fiber-based foreign matter, may be input as the foreign matter amount variable.

In the above embodiments, the particle size of the foreign matter is classified into three ranges, but it may be classified into two ranges or four or more ranges. Furthermore, it is not necessary to classify the amount of foreign matter by the particle size.

Instead of treating the number of particles of the foreign matter contained in the oil per unit volume as the foreign matter amount variable, a total volume or a total weight of the foreign matter contained in the oil per unit volume may be adopted as the foreign matter amount variable.

For example, as the shifting number variable, a value other than the number of times of shifting SN of the automatic transmission 30 may be adopted. As a specific example, the number of times of engagement of a specific engaging element among the engaging elements constituting the automatic transmission 30, for example, the first clutch C1, may be adopted as the shifting number variable.

For example, the traveling distance MI and the traveling time RT of the vehicle 100 have a certain degree of correlation with each other. Therefore, only one of the traveling distance MI and the traveling time RT may be adopted as the input variable.

For example, as the input variables, the amount of foreign matter contained in the oil, the number of times of shifting SN, the traveling distance MI, and the traveling time RT are not necessarily required, and may be omitted as appropriate. That is, as long as the input variables include at least the color variable and the hydrogen ion variable, the degree of deterioration of oil can be estimated with appropriate accuracy.

About Output Variable

In the first embodiment and the second embodiment, the output variable is not limited to the example of the above embodiments. For example, as the deterioration of the oil stored in the oil pan 68 progresses, a remaining traveling time that is a time that the vehicle 100 can travel before the replacement of the oil stored in the oil pan 68 with new oil tends to be shorter. Therefore, as the output variable, the variable indicating the remaining traveling time may be adopted. In this case, the output variable is a variable indicating the replacement timing at which the oil needs to be replaced.

For example, as the output variable, a variable indicating the degree of deterioration of oil may be adopted. As a specific example, when the state of oil that has not deteriorated is "0" and the state of oil that has deteriorated and needs to be replaced is "1", a variable that changes between "0" and "1" may be adopted as the output variable indicating the degree of deterioration of oil. With this configuration, it is easy to objectively grasp the degree of deterioration of oil as a numerical value. Note that "0" is an example of a first value indicating a state in which the oil has not deteriorated, and "1" is an example of a second value indicating a state in which the oil needs to be replaced.

About Mapping

In the first embodiment and the second embodiment, the activation function of the mapping is merely an example, and the activation function of the mapping may be changed.

In the first embodiment and the second embodiment, as the neural network, a neural network having one intermediate layer is exemplified, but the number of intermediate layers may be two or more.

In the first embodiment and the second embodiment, as the neural network, a fully connected feedforward neural network is exemplified, but the neural network is not limited to this. For example, as the neural network, a recurrent neural network may be adopted.

In the first embodiment and the second embodiment, the function approximator serving as the mapping is not limited to the neural network. For example, the function approximator may be a regression equation without an intermediate layer.

About Execution Device

In the first embodiment, the execution device is not limited to the one including the CPU 291 and the ROM 293 to execute software processes. As a specific example, the execution device may include a dedicated hardware circuit (for example, an application specific integrated circuit (ASIC)) that executes hardware processes in place of at least part of the software processes executed in the above embodiment. That is, the execution device only needs to have any of the following configurations (a) to (c):

(a) a configuration including a processing device that executes all of the above processes according to a program and a program storage device such as a ROM for storing the program;

(b) a configuration including a processing device that executes part of the above processes according to a program, a program storage device, and a dedicated hardware circuit that executes the remaining processes; and (c) a configuration including a dedicated hardware circuit that executes all of the above processes. Here, the above configurations may have a plurality of software execution devices including a processing device and a program storage device and a plurality of dedicated hardware circuits. The same applies to the second embodiment.

About Oil

In the first embodiment and the second embodiment, the oil supplied to the automatic transmission 30 has been exemplified as the oil for estimating the degree of deterioration, but the applicable embodiment is not limited to this. For example, assume that instead of the automatic transmission 30, the vehicle 100 is provided with a manual transmission that changes the gear stage by the operation of the driver and the manual transmission is supplied with oil from the hydraulic device. In this configuration, the degree of deterioration of oil supplied from the hydraulic device to the manual transmission may be estimated. In this case, the manual transmission serves as the transmission.

Further, for example, assume that instead of the automatic transmission 30, the vehicle 100 is provided with a continuously variable transmission that changes the gear ratio steplessly in accordance with the pressure of oil supplied from the hydraulic device. In this configuration, the degree of deterioration of oil supplied from the hydraulic device to the continuously variable transmission may be estimated. In this case, the continuously variable transmission serves as the transmission.

Further, for example, not only oil supplied to the transmission but also oil supplied from the hydraulic device to the internal combustion engine to circulate in each part of the internal combustion engine may be estimated in terms of degree of deterioration. That is, the technology of the present disclosure can be applied to any kind of oil used in a vehicle.

About Vehicle

In the first embodiment and the second embodiment, a so-called series-parallel hybrid vehicle has been exemplified as the vehicle, but the vehicle is not limited to this. For example, the vehicle may be a series hybrid vehicle or a parallel hybrid vehicle.

In the first embodiment and the second embodiment, the vehicle is not limited to the vehicle including an internal combustion engine and a motor generator. For example, the vehicle may be a vehicle having an internal combustion engine and no motor generator. Further, for example, the vehicle may be a vehicle having a motor generator and no internal combustion engine.

What is claimed is:

1. A deterioration estimation device that is applied to a vehicle equipped with a hydraulic device configured to supply oil and that is configured to estimate a degree of deterioration of the oil, the deterioration estimation device comprising:

a storage device configured to store mapping data defining a mapping that outputs an output variable indicating the degree of deterioration of the oil when an input variable is input, the mapping including, as the input variable, a color variable that is a variable indicating a color of the oil and a hydrogen ion variable that is a variable indicating a hydrogen ion concentration of the oil; and an execution device configured to execute an acquisition process that is a process of acquiring the input variable and a calculation process of inputting the input variable acquired through the acquisition process to the mapping to output a value of the output variable, wherein the mapping includes a first foreign matter amount variable and a second foreign matter amount variable as the input variable, the first foreign matter amount variable indicating an amount of foreign matter having a particle size within a first range determined in advance, out of foreign matter contained per unit volume of the oil, and the second foreign matter amount variable indicating an amount of foreign matter having a particle size within a second range determined in advance as a range that is different from the first range, out of the foreign matter contained per unit volume of the oil.

2. The deterioration estimation device according to claim 1, wherein:

the vehicle includes a transmission configured to be supplied with oil from the hydraulic device; and the mapping includes, as the input variable, a shifting number variable indicating a number of times of shifting of the transmission since the oil is supplied to the vehicle.

3. The deterioration estimation device according to claim 1, wherein the mapping includes, as the input variable, a traveling distance variable indicating a traveling distance of the vehicle since the oil is supplied to the vehicle.

4. The deterioration estimation device according to claim 1, wherein the mapping includes, as the input variable, a traveling time variable indicating a traveling time that a vehicle speed of the vehicle is higher than zero since the oil is supplied to the vehicle.

5. The deterioration estimation device according to claim 1, wherein the output variable is a variable indicating a replacement timing at which the oil needs to be replaced.

6. The deterioration estimation device according to claim 1, wherein the output variable is a variable that changes between a first value and a second value, the first value being a value that indicates a state in which the oil has not deteriorated, and the second value being a value that indicates a state in which the oil needs to be replaced and that is different from the first value.

7. The deterioration estimation device according to claim 1, wherein the input variable includes a third foreign matter amount variable indicating an amount of foreign matter having a particle size within a third range determined in advance as a range that is different from the first range and the second range, out of the foreign matter contained per unit volume of the oil.

8. A deterioration estimation method that is applied to a vehicle equipped with a hydraulic device configured to supply oil and that is for estimating a degree of deterioration of the oil using a deterioration estimation device, the deterioration estimation method comprising inputting, as an input variable, a color variable that is a variable indicating a color of the oil, a hydrogen ion variable that is a variable indicating a hydrogen ion concentration of the oil, a first foreign matter amount variable and a second foreign matter amount variable to the deterioration estimation device to calculate a value of an output variable, the deterioration estimation device being configured to store mapping data defining a mapping that outputs the output variable indicating the degree of deterioration of the oil when the input variable is input, wherein the first foreign matter amount variable indicates an amount of foreign matter having a particle size within a first range determined in advance, out of foreign matter contained per unit volume of the oil, and the second foreign matter amount variable indicates an amount of foreign matter having a particle size within a second range determined in advance as a range that is different from the first range, out of the foreign matter contained per unit volume of the oil.

9. A non-transitory storage medium, as a deterioration estimation device that is applied to a vehicle equipped with a hydraulic device configured to supply oil and that is configured to estimate a degree of deterioration of the oil, storing instructions that are executable by one or more processors and that cause the one or more processors to:

acquire, as an input variable, a color variable that is a variable indicating a color of the oil, a hydrogen ion variable that is a variable indicating a hydrogen ion concentration of the oil, a first foreign matter amount variable and a second foreign matter amount variable; and input the acquired input variable to the deterioration estimation device to calculate a value of an output variable, the deterioration estimation device being configured to store mapping data defining a mapping that outputs the output variable indicating the degree of deterioration of the oil when the input variable is input, wherein the first foreign matter amount variable indicates an amount of foreign matter having a particle size within a first range determined in advance, out of foreign matter contained per unit volume of the oil, and the second foreign matter amount variable indicates an amount of foreign matter having a particle size within a second range determined in advance as a range that is different from the first range, out of the foreign matter contained per unit volume of the oil.

* * * * *